United States Patent [19]

Stirling

[11] 4,036,969
[45] July 19, 1977

[54] 2,12-DIOXO-7-HYDROXYMETHYL-9-PHENYL-1-AZA-5,8,11-TRIOXOTETRACYCLO[9.2.0.0⁶,¹³0.⁶,⁹]TRIDECANE

[75] Inventor: Irene Stirling, Worcester Park, England

[73] Assignee: Beecham Group Limited, England

[21] Appl. No.: 695,102

[22] Filed: June 11, 1976

[30] Foreign Application Priority Data

Dec. 15, 1975 United Kingdom ............... 51200/75

[51] Int. Cl.² .................... C07D 498/04; A61K 31/42
[52] U.S. Cl. ............................. 424/272; 260/307 FA; 424/246; 424/271
[58] Field of Search .................. 260/307 FA; 424/272

[56] References Cited

U.S. PATENT DOCUMENTS 3,948,927  4/1976  Wolfe ............................ 260/307 FA

*Primary Examiner*—Raymond V. Rush

*Attorney, Agent, or Firm*—Jacobs & Jacobs

[57] ABSTRACT

Compounds of the formula

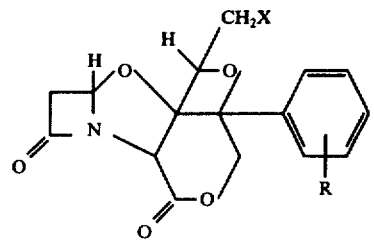

wherein
R is methyl, ethyl, trifluoromethyl, methoxy, ethoxy, nitro, hydrogen or halogen, and
X is hydroxy or hydrogen, are useful as β-lactamase inhibitors.

3 Claims, No Drawings

2,12-DIOXO-7-HYDROXYMETHYL-9-PHENYL-1-AZA-5,8,11-TRIOXOTETRACYCLO[9.2.0.0^{6,13}0.^{6,9}]-TRIDECANE

The present invention relates to novel β-lactam containing compounds, to their preparation and to compositions containing them, the said β-lactam containing compounds possessing β-lactamase inhibiting activity.

Belgium Pat. No. 827,926 discloses inter alia clavulanic acid which is the compound of the formula (I):

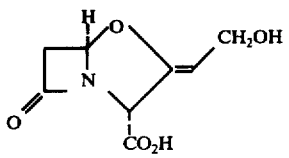

and its salts and esters. Clavulanic acid is a β-lactamase inhibitor and an antibacterial agent.

We have now discovered a distinct group of compounds which have β-lactamase inhibitory activity.

Accordingly, the present invention provides compounds of the formula (II):

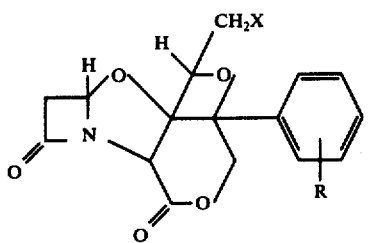

wherein R is a methyl, ethyl, trifluoromethyl, methoxy, ethoxy or nitro group or a hydrogen or halogen atom and X is a hydroxy group or a hydrogen atom.

Suitably R is hydrogen or methyl, ethyl or trifluoromethyl group.

Preferably R is a hydrogen atom.

In a composition aspect, the present invention provides a pharmaceutical composition which comprises a compound of the formula (II) as hereinbefore described. Such compositions will also comprise a pharmaceutically acceptable carrier.

The composition of this invention will normally be adapted for administration to humans and other mammals, for example, in conventional modes of treatment of diseases of the urinary tract, respiratory system and soft tissues as well as diseases such as otitis media and mastitis and the like.

Suitable forms of the composition of this invention include tablets, capsules, creams, syrups, suspensions, solutions, reconstitutable powders, and sterile forms suitable for injection or infusion may be used. Such compositions may contain conventional pharmaceutically acceptable materials such as diluents, binders, colours, flavours, preservatives, disintegrants and the like in accordance with conventional pharmaceutical practice.

The compound of formula (II) may be present in the composition as sole therapeutic agent or it may be present together with other therapeutic agents such as a penicillin or cephalosporin antibiotic. Thus, suitable penicillin or cephalosporin antibiotics for inclusion in the composition of this invention include benzylpenicillin, phenoxymethyl-penicillin, carbenicillin, methicillin, propicillin, hetacillin, ampicillin, amoxycillin, ticarcillin, cephaloridine, cephalothin, cephalexin, cephamandole, cephaloglycine, cefuroxime, and in vivo hydrolysable esters of compounds such as the phenyl and indanyl esters of carbenicillin and ticarcillin, the acetoxymethyl ester of benzyl-penicillin and the pivaloyloxymethyl and phthalidyl esters of ampicillin and amoxycillin.

When present in a pharmaceutical composition together with a penicillin or cephalosporin, the ratio of the compound of formula (II) present to penicillin or cephalosporin present may be from, for example, 10:1 to 1:3 and advantageously may be from 5:1 to 1:2, for example, 3:1 to 1:1.

The total quantity of antibacterial agents present in any unit dosage form will normally be between 50 and 1500 mg and will usually be between 100 and 1000 mg. However, injectable or infusable compositions may contain greater quantities if desired, for example, 4 g or more of active material.

Normally between 50 and 6000 mg of the compositions of the invention will be administered each day of treatment but more usually between 500 and 3000 mg of the compositions of the invention will be administered per day. However, for the treatment of severe systemic infections or infections of particularly intransigent organisms, higher doses may be used in accordance with clinical practice.

The present invention also provides a process for the preparation of a compound of the formula (II) as hereinbefore defined which process comprises the ultra-violet irradiation of a compound of the formula (III):

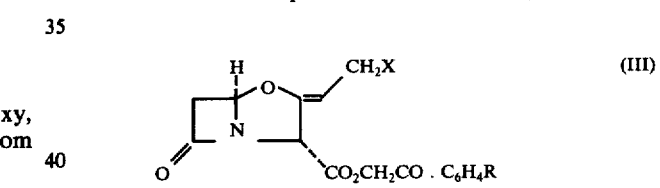

wherein R and X are as defined in relation to formula (II). This reaction is normally carried out in a degassed organic solvent such as benzene, carbon tetrachloride, acetonitrile or other conventional solvents and frequently under an inert atmosphere of nitrogen or argon.

This reaction is normally carried out at ambient temperature for the sake of convenience but any non-extreme temperature may be used, for example, −20° to +80° C, although moderate temperatures, for example 15° to 35°, are preferred.

In accordance with conventional practice a photosensitizer may be included if desired. Thus, such agents as dibenzyl, iodine, acetophenone, benzophenone and the like may be included.

Wide or narrow spectrum u.v. may be employed to produce photolytic isomerisation of the compound of the formula (III). We have found that 40 watt Hanovia low pressure mercury lamps and 450 watt Hanovia medium pressure mercury lamps give satisfactory results (obtained from Hanovia Lamps Ltd., Slough, Buckinghamshire, England). In use, such lamps may employ a water-cooling jacket of silica.

When a compound of the formula (III) is irradiated with ultraviolet light the compound of the formula (II) may be formed in admixture with the starting material or with a number of other products. This mixture may be separated by conventional means, for example, by chromatography. We have found a suitable means of separating compounds of the formula (II) to be column chromatography on silica gel eluting with an ethyl acetate/cyclohexane mixture.

The following examples are illustrative of the invention:

EXAMPLE 1

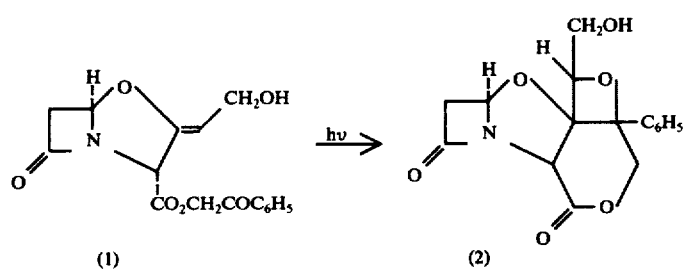

A dilute solution of phenacyl clavulanate (1) in dry benzene was photolysed under nitrogen for 3 hours. The solvent was removed and the residue was chromatographed on silica gel (elution with ethyl acetate/cyclohexane) to give two products; the more polar of which was unreacted starting material. The less polar product was examined by h.p.l.c. and found to be a mixture of two compounds which were separated by preparative h.p.l.c. The first eluted compound was the oxetane (2). M.p. 188° [from ethyl acetate/petroleum ether (60°- 80°)]. The structure of this compound was confirmed by X-ray crystallography.

EXAMPLE 2

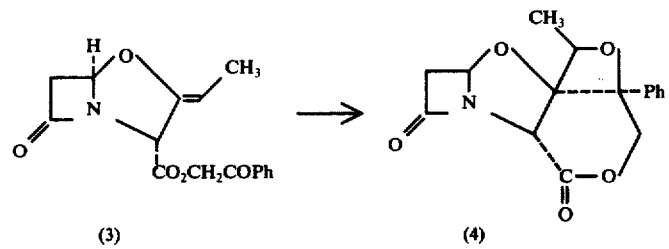

A solution of phenacyl deoxyclavulanate (3) in dry benzene was photolysed, for 5 hours, in an inert atmosphere in a Reading Photochemical Reactor using two 40 watt low pressure lamps. The solvent was removed and the residue was chromatographed on silica gel (elution with cyclohexane/ethyl acetate) to give two products. The product eluted first was the oxetan (4) which crystallised from ethyl acetate-petroleum ether (60°-80°) as colourless needles in 33 percent yield; m.p. 228°.

What is claimed is:

1. A compound of the formula (II):

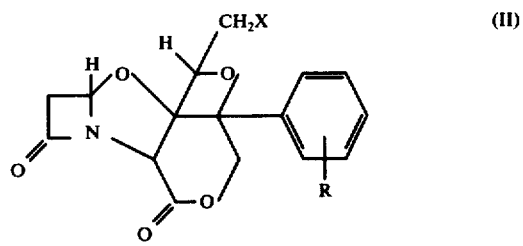

wherein R is hydrogen and X is hydroxy.

2. A pharmaceutical composition useful for effecting β-lactamase inhibition in humans and other mammals which comprises a β-lactamase inhibitory amount of the compound of claim 1 in combination with a pharmaceutically acceptable carrier.

3. A process for the preparation of the compound of claim 1 which process comprises the ultra-violet irradiation of a compound of the formula (III):

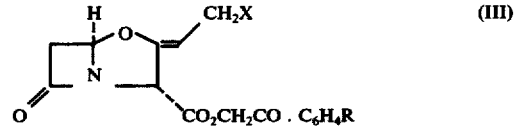

wherein R is hydrogen and X is hydroxy, until a substantial amount of the compound of claim 1 is produced and isolating said product.

* * * * *